United States Patent [19]

Lowthian

[11] Patent Number: 4,634,437
[45] Date of Patent: Jan. 6, 1987

[54] ANTI-KINK DEVICE FOR A FLEXIBLE URINE COLLECTOR

[75] Inventor: Peter T. Lowthian, Watford, England

[73] Assignee: Simpla Plastics Limited, Cardiff, Wales

[21] Appl. No.: 696,136

[22] Filed: Jan. 29, 1985

[30] Foreign Application Priority Data

Jan. 31, 1984 [GB] United Kingdom ............... 8402455

[51] Int. Cl.$^4$ ............................................. A61M 1/00
[52] U.S. Cl. .................................. 604/323; 604/335; 604/350; 128/767
[58] Field of Search ....................... 604/317, 322–326, 604/335, 350; 248/95; 128/760, 766, 767, 769, DIG. 24; 383/33, 44, 46, 47

[56] References Cited

U.S. PATENT DOCUMENTS

| 3,724,461 | 4/1973 | Eisenberg | 604/322 |
| 4,462,510 | 7/1984 | Steer et al. | 604/248 |
| 4,501,584 | 2/1985 | Cianci et al. | 604/322 |
| 4,534,766 | 8/1985 | Steer et al. | 604/323 |
| 4,562,984 | 1/1986 | Sherlock | 128/DIG. 24 |

FOREIGN PATENT DOCUMENTS

| 270128 | 5/1927 | United Kingdom . |
| 871862 | 7/1961 | United Kingdom . |
| 1474435 | 6/1975 | United Kingdom . |
| 2084879A | 4/1982 | United Kingdom . |
| 2092896A | 8/1982 | United Kingdom . |
| 2118525 | 11/1983 | United Kingdom ............... 604/322 |

Primary Examiner—C. Fred Rosenbaum
Assistant Examiner—J. L. Kruter
Attorney, Agent, or Firm—Flynn, Thiel, Boutell & Tanis, P.C.

[57] ABSTRACT

A device for preventing or hindering obturation of an inlet valve of a urine collector bag, the device being a trifurcate member of unitary construction being generally planar and incorporated in the bag. The central limb of the device is curved in cross-section and seats the valve so that even when the bag or valve is crushed, twisted or shortened, the valve remains open, being supported and strengthened by the device. The limbs of the device are situated at the sides of the bag in use.

14 Claims, 4 Drawing Figures

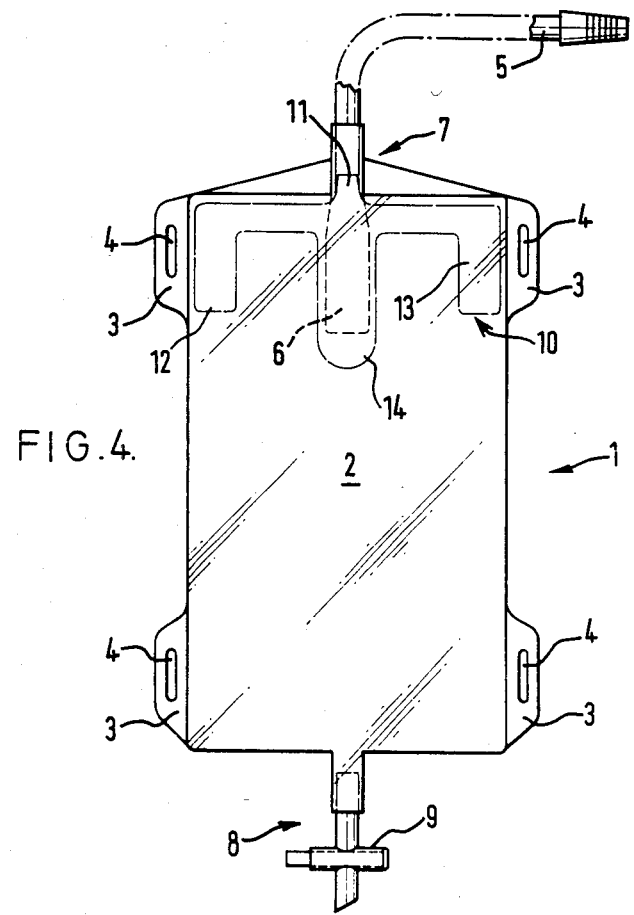

ANTI-KINK DEVICE FOR A FLEXIBLE URINE COLLECTOR

FIELD OF THE INVENTION

The invention relates to urine collection, particularly to a device for preventing or hindering obturation of inlet means of a flexible collector for urine, a flexible collector for urine, and a urinary drainage system.

BACKGROUND OF THE INVENTION

Urine collectors are often in the form of flexible plastic bags to which urine is fed via a plastic tube connecting the bag directly or indirectly to a user of the bag. The tube leads to a non-return valve of the collapsible tube kind which is within the bag. The bag is generally affixed as by straps to a leg of the user so that in many cases the bag is not in evidence at all and the user is completely mobile.

Because the inlet tube, bag and non-return valve are flexible when the user is using the bag strapped to a part of the leg such as the thigh, skin or calf, normal movements of the user can result in the tube, and the non-return valve being blocked or partially blocked (restricted) owing to bending, kinking or twisting or the inlet tube, or "bunching" of the material of the bag and/or of the non-return valve at the top of the bag.

These bags are used with catheters usually, and "kinking" of the non-return valve causes back-pressure in an in-dwelling catheter for both sexes or a condom-catheter for males. This then results in a build-up of pressure in the bladder. When sufficient volume of urine is contained in the bladder, stretch sensors of the bladder cause it to contract spontaneously so expelling urine. This then by-passes an in-dwelling catheter, and some urine leaks out. However, there is still pressure in the bladder and the back pressure can cause reflux of urine to the kidneys with consequent risk of infection and/or kidney damage. The plasma membrane of the bladder itself can also be damaged, with consequent infection risk.

A condom-catheter can also be forced off its seat owing to pressure-build up, with consequent discomfort and infection risk.

It is accordingly among the objects of the invention to seek to mitigate these disadvantages.

According to the invention there is provided a device for preventing or hindering obturation of inlet means of a flexible collector for urine, comprising a relatively rigid body adapted to be mounted in the collector adjacent the inlet means and to prevent or hinder obturation thereof so that flow of liquid into the collector is permitted.

The body may be generally planar. This provides for ease of manufacture, for example by moulding when the device is made of plastic.

The generaly planar body may include a part curved out of the plane of the body. This allows accommodation of a non-return valve in use.

The body may be adapted by a projecting tongue means to be mounted in the collector adjacent the inlet means.

The device may be moulded in one piece from plastic.

According to a second aspect of the invention there is provided a flexible collector for urine, comprising an inlet means, an outlet means, and a device as hereinbefore defined mounted therein adjacent the inlet means so as to prevent or hinder obturation thereof so that flow of liquid into the collector is permitted.

The inlet means may comprise an inlet tube leading to a flexible non-return valve within the collector, and the device may lie adjacent part of the tube and extending over the non-return valve.

The device may be trifurcated and the central limb may extend over the non-return valve.

The central limb may be curved in transverse cross-section whereby to receive and support the non-return valve when liquid flows therethrough.

The lateral limbs of the device may be planar each one being adjacent a respective side of the collector.

The lateral limbs of the device may be shorter than the central limb.

The device may extend over part of the length of the collector, preferably over about 30% of the length of the collector.

According to a third aspect of the invention there is provided a urinary drainage system including a urine collector as hereinbefore defined.

The invention is diagrammatically illustrated, by way of example, with reference to the accompanying drawings.

BRIEF DESCRIPTION OF DRAWINGS

FIG. 4 shows a schematic plan view to the same scale as that of FIG. 1, of a flexible urine collector incorporating the device shown in FIGS. 2 and 3.

DETAILED DESCRIPTION

Figure 1:
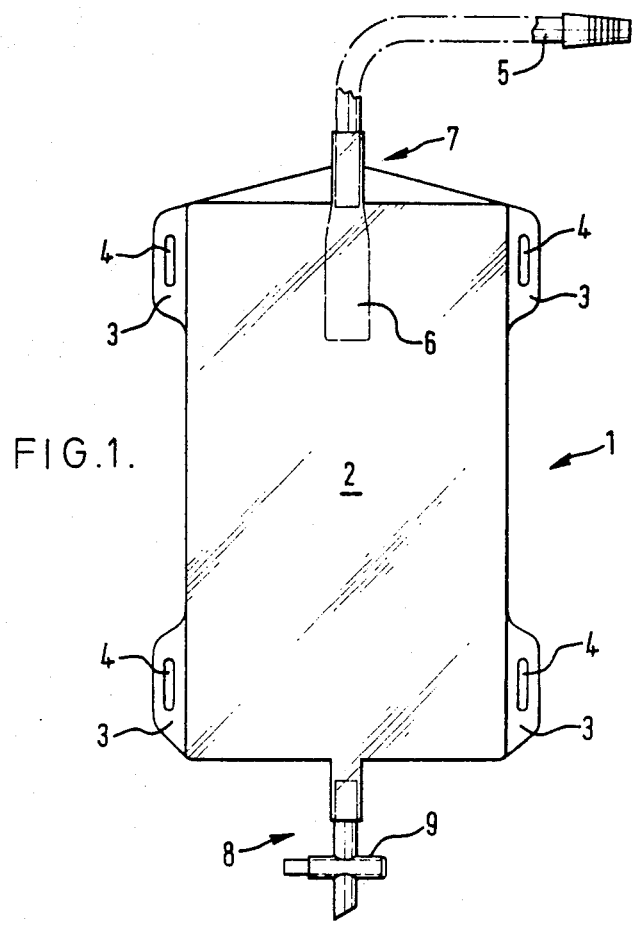
FIG. 1 is a schematic plan view of a known flexible collector for urine.

Referring to the drawings, the urine collector 1 shown in FIG. 1 is a known collector which includes a flexible plastics bag 2 which is generally oblong and is for wear on a user's leg. To that end the bag has wings 3 with eyes 4 through which straps (not shown) can be passed to hold the bag 2, the straps then being passed round the user's leg and secured. The bag 2 is connected with a user's bladder indirectly via a tube 5 which passes into the bag to connect with a non-return valve 6 of the collapsing tube kind. The part of the tube 5 in and adjacent the bag 2, and the non-return valve 6 comprise inlet means 7 of the bag. The bag 2 has an outlet 8 with a simple slide tap 9 which can be operated with one hand.

The bag 2 is very flexible or pliable so that it can be accommodated on a user's leg unobtrusively and with little discomfort. However, because of this pliability, the bag 2 can ruck up or "concertina" longitudinally, so causing the non-return valve 6, also plastic and pliable, to do the same, with the result that blockage can occur. Also, the bag 2 can be twisted because of movement of the leg of the user, and this can also result in blocking. Finally, the tube 5 can be twisted or bent, or become kinked, particularly at or adjacent its entry into the bag 2. This can also result in blocking of urine flow into the bag or collector, with discomfort to the user, and the possibility of retrograde infection.

Figures 2, 3:
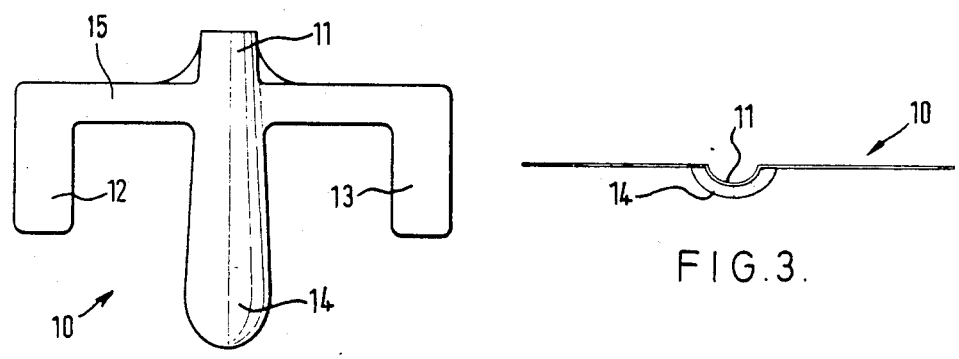
FIGS. 2 and 3 are respective elevational and plan views, to an enlarged scale, of a device according to the invention for preventing or hindering obturation of inlet means of the collector of FIG. 1.

A device 10 embodying the invention is shown in FIGS. 2 to 4, and it prevents or hinders obturation of the inlet means 7 of the bag, by increasing the rigidity thereof.

The device 10 is moulded from plastics in one piece, and is of trifurcate construction, and is relatively stiff, though still flexible, as compared to the bag 2. The device 10 has a tongue means 11 whereby it can be secured to the tube 5 adjacent the entry to the bag 2, two lateral arms 12 and 13 which extend in the bag 2 adjacent the sides thereof, and a central limb 14, longer than the lateral limbs 12 and 13, which overlies the non-return valve 6 in use, as shown in FIG. 4. These limbs all project downwardly from a transverse support or bar 15, and the tongue 11 projects upwardly therefrom. Moreover, the central limb 14 is curved as considered in cross-section so that the non-return valve 6 lies within the lateral boundaries of the limb 14 and is supported thereby when fluid flows through the valve 6, which assumes a generally tubular configuration when fluid flow takes place. The limb 14 thus acts as a shield and as a guide for the non-return valve 6, by maintaining the non-return valve 6 elongate and shielding it against lateral crumpling. Also, as the limb 14 is longer than the non-return valve, the valve 6 is protected or shielded against longitudinal crumpling or concertinaing, and is also strengthened by the device 10 which also acts as a strengthener.

The device 10 also prevents bending or twisting of the inlet tube 5, so that that tube 5 cannot become kinked or otherwise obturated, however the bag and tube are twisted or bent. The tongue means 11 ensures this as it is secured to the outside of the tube 5, which is received within the curved part of the tongue means 11, which is aligned with the central limb 14 as shown.

The lateral limbs 12 and 13 are planar to prevent lateral collapsing of the bag or twisting thereof, so that the device 10 as a whole retains the dimensional integrity of the bag 2 in use and permits unblocked flow of urine into the bag.

The device 10 extends over about 30% of the length of the bag and is generally planar in plan, only the limb 14 and tongue means 11 projecting out of the plane of the device.

The device is only secured by the tongue means 11.

The device 10 is not secured to any other part of the bag and merely lies in the bag as shown, overlying the non-return valve 6, in other words the device 10 is external of the valve as considered in relation to the user. The valve 6 is thus between the user and the device 10 in use.

It is envisaged that the tube 5 and device 10 will be secured together via the tongue means 11 as by a specific connector such as a rubber or plastics band, or by welding, so providing the completed collector 1 shown in FIG. 4.

It will be understood that the whole 1 as shown in FIG. 4 would be put up for sale in a sterilised pack.

The collector 1 may be part of a urine drainage system, not shown.

It will be understood that the invention above described and shown in the drawings may be modified. For example, the central limb 14 may be planar. Also, the device 10 would be of any other convenient shape other than trifurcate, for example triangular. The device 10 and the non-return valve may also be secured together as by welding, in an alternate construction method, prior to assembly with the bag. The device and valve thus form an integral unit prior to assembly, and this simplifies the construction of the whole system.

I claim:

1. A flexible collector arrangement for urine, comprising:
   (i) a flexible baglike collector for urine;
   (ii) said collector having an inlet and outlet means for permitting urine to be respectively supplied to and removed from said collector;
   (iii) a flexible non-return valve means in the collector adjacent said inlet means;
   (iv) a device mounted wholly within the collector, adjacent said valve means for preventing obturation thereof, said device comprising:
      (a) a trifurcate body member having two lateral limbs and an intermediate limb;
      (b) said two lateral limbs each extending along respective opposite sides of the collector and longitudinally thereof from the inlet means towards the outlet means;
      (c) said intermediate limb being at least as long as and overlying said non-return valve means, said intermediate limb also being substantially parallel to the two lateral limbs and extending from the inlet means toward the outlet means; and
      (d) a tongue means projecting opposite and away from the intermediate limb and being secured to said inlet means, whereby the body member is secured wholly within the bag and the intermediate limb obviates rucking of the non-return valve means for preventing obturation thereof.

2. A flexible collector arrangement as defined in claim 1, wherein the limbs lie substantially within the same plane.

3. A flexible collector arrangement as defined in claim 2, wherein the intermediate limb is curved in a direction transverse to its length whereby to receive and support said non-return valve means.

4. A flexible collector arrangement as defined in claim 3, wherein the intermediate limb is longer than both the lateral limbs and the valve means.

5. A flexible collector arrangement as defined in claim 1, wherein the intermediate limb is curved in a direction transverse to its length whereby to receive and support said non-return valve means.

6. A flexible collector arrangement as defined in claim 5, wherein the intermediate limb is longer than the lateral limbs.

7. A flexible collector arrangement as defined in claim 1, wherein the tongue means is curved in a direction transverse to its length, whereby to receive a tube comprising said inlet means.

8. A flexible collector arrangement as defined in claim 1, wherein the inlet means includes an inlet opening formed in an end of the baglike collector, said inlet opening being adapted to receive therein the discharge end of a urine supply tube.

9. A flexible collector arrangement according to claim 8, wherein said outlet means includes an outlet opening associated with an end of said baglike collector and having a closable valve structure associated therewith.

10. A flexible collector arrangement according to claim 9, wherein said inlet and outlet openings are respectively associated with upper and lower ends of the baglike collector, and wherein said tongue means projects into said inlet opening and is transversely curved for accommodating the supply tube.

11. A flexible collector arrangement according to claim 10, wherein the limbs project downwardly from a transverse support, said tongue means projecting upwardly from said transverse support in substantial alignment with said intermediate limb, and wherein said intermediate limb is transversely curved throughout its length to receive and support the non-return valve means.

12. A flexible collector arrangement as defined in claim 1, wherein said limbs all project downwardly from a transverse support, and wherein said tongue means projects upwardly from said transverse support in substantial alignment with said intermediate limb.

13. A flexible collector arrangement according to claim 12, wherein said body member is constructed in one piece of a plastics material which is relatively stiff.

14. A flexible collector arrangement according to claim 1, wherein said body member is constructed in one piece of a plastics material which is relatively stiff.

* * * * *